United States Patent [19]

Périlhou

[11] 4,075,482
[45] Feb. 21, 1978

[54] GAMMA-RADIATION TOMOGRAPHY SYSTEM

[75] Inventor: Jean Robert Périlhou, Bourg la Reine, France

[73] Assignee: U.S. Philips Corporation, New York, N.Y.

[21] Appl. No.: 648,398

[22] Filed: Jan. 12, 1976

[30] Foreign Application Priority Data

Jan. 17, 1975 France .................. 75 01471

[51] Int. Cl.² .................. G01T 1/164; G01T 1/20
[52] U.S. Cl. .................. 250/363 S; 250/445 T
[58] Field of Search .................. 250/363 S, 445 T

[56] References Cited

U.S. PATENT DOCUMENTS

3,329,814  7/1967  Anger .................. 250/363 S
3,961,186  6/1976  Leunbach .................. 250/363 S Primary Examiner—Archie R. Borchelt
Attorney, Agent, or Firm—Frank R. Trifari

[57] ABSTRACT

Each point which can be detected in the tomography plane is localized as the intersection of at least two intersecting "examination lines", each of which is defined by the position of two detectors whose inputs are coupled to a time coincidence circuit. The time coincidence circuits for each of the points per pair of intersecting examination lines are coupled to a contrast circuit which supplies the product of the numbers of strikes detected in time coincidence during a time interval T. After each time interval T, the contrast circuit actuates a monostable circuit which powers a microincandescent lamp for a period of time which is a function of this product.

12 Claims, 5 Drawing Figures

GAMMA-RADIATION TOMOGRAPHY SYSTEM

The invention relates to a tomography system utilizing gamma-radiation, for example a system designed for making a tomograph — in a properly defined plane of examination — of a patient (or of an object) after a radio-active, positron-emissive ($\beta+$) matter has been injected into the body of the patient.

The positron-(positive electrons)emissive radioisotopes can be of special importance for the image formation needed to achieve a medical diagnosis; this is because these radioisotopes give off little energy in the tissue and disappear by combination with a negative electron ($\beta-$), pairs of $\gamma$-rays then being generated at the point of annihilation with an energy of 0.51 meV, the said rays being oriented in mutually opposed directions.

If two detectors are provided, i.e. one detector arranged in the path of each of the two rays, two electrical signals are generated which can be converted, by means of a summing device, into a usable signal if summing takes place only if the signals of the two detectors coincide in time within very narrow limits; as the time permitted for the coincidence time is smaller, the selection of the two gamma-rays will be more accurate as regards incidental parasitic radiation. This special property is utilized in positron cameras. The heavy collimator which is made of lead (or another hevy metal) and which is required for the cameras normally used for gammagraphy, such as the Anger camera, can thus be dispensed with.

There are positron cameras which comprise a camera of the Anger type which is coupled to focussing detectors which are arranged on the other side of the body to be examined and which serve, by detecting the gamma-ray whose direction opposes that of the ray detected by the camera of the Anger type, to determine the coincidence time, i.e. the evaluation of the detection of a "strike" (the frequency of the strikes which each correspond to the annihilation of a B+ in a point of the field of examination determines the radio-activity in this point). The images produced by a device of this kind are usually rather coarse; this thus far has impeded development. It has also been attempted to use two Anger cameras, one arranged opposite the other, but because of the substantial thickness of the detector required for efficiently absorbing the $\gamma$-rays, these systems have a low efficiency and count an insufficient number of strikes. This number is smaller because the time required for calculating the positioning of the cameras does not permit a given number of strikes to be exceeded.

Other gamma-graphy systems have also been proposed which utilize detection crystal lattices for counting the numerous strikes. For practical reasons, the crystal lattices are flat and are manufactured either in the form of two oppositely arranged columns (in this case the field of examination is scanned by displacement of the columns) or in the form of two mosaics which are also oppositely arranged. An embodiment of the latter version in the "MGH Positron Camera" described in "Instrumentation in Nuclear Medicine" volume 2, pages 148–156. Each mosaic comprises 127 crystals which are arranged to be staggered with respect to eac other in nine columns of seven crystals each, alternating with eight columns of eight crystals each; this mosaic is connected to a network of 72 photomultipliers arranged in the form of nine columns of eight photomultipliers, so that each crystal is "seen" by two photomultipliers, each photomultiplier seeing four crystals. Electronic circuits enable the detection of two simultaneously received rays: on the one side by a relevant crystal of a mosaic and on the other side by one of the 25 crystals of the other mosaic which is oppositely arranged. For each crystal 25 different examination lines are thus defined; the geometrical structure corresponding to this definition exhibits four planes which are parallel to the mosaics, which are situated at 2/10, 4/10, 6/10 and 8/10 part of the distance between the two mosaics, and for which the examination lines form, by way of their points of intersection with these planes, a uniform network of "examination points". If an image is frmed by treatment of the data in coincidence, it can thus in principle be assumed that the detected "strikes" originate from a single plane, i.e. the one of the four above defined planes which is situated in the body to be examined.

These two systems, utilizing detection crystal lattices, require a rather complex data processing unit.

The present invention relates to a gamma-ray tomography system, the tomographic effect being based on a difference in contrast, expressed in numbers of strikes or in current during imaging, between zones wherein a radio-active source is exactly situated in the tomography plane and zones where this is not the case. This is effected to isolate the most radio-active zones by a striking contrast.

The system in accordance with the invention offers the additional advantage that it results in an apparatus of low weight and small volume, whereby an image can be directly formed and which has a comparatively low cost price.

The gamma-radiation tomography system in accordance with the invention enables the direct display of the image of a radio-active body in a defined plane of examination PA of the type which defines $n$ examination points which are situated on examination lines which coincide with the feasible paths of pairs of $\gamma$-rays which originate from the said $n$ points and which are detected in time coincidence by two detectors which are arranged at the ends of each of the said lines, is characterized in that each of the $n$ examination points is localised at the point of intersection of at least two intersecting examination lines, the strikes which are detected in time coincidence by the pairs of detectors intended for the intersecting examination lines in one and the same examination point being treated in one of $n$ contrast circuits which serve for the $n$ points and which are adapted such that they supply an equivalent of the product of the numbers of strikes detected in time coincidence, means being provided for directly displaying each of the $n$ points of the plane by the direct use of an output signal of each of the $n$ contrast circuits.

A number of preferred embodiments in accordance with the invention will be described in detail hereinafter with reference to the drawing.

The number of detectors and the distance between the detectors, can be chosen at random. The particular number of detectors and the distance therebetween in the figures has been chosen only for the sake of clarity.

Figure 1:
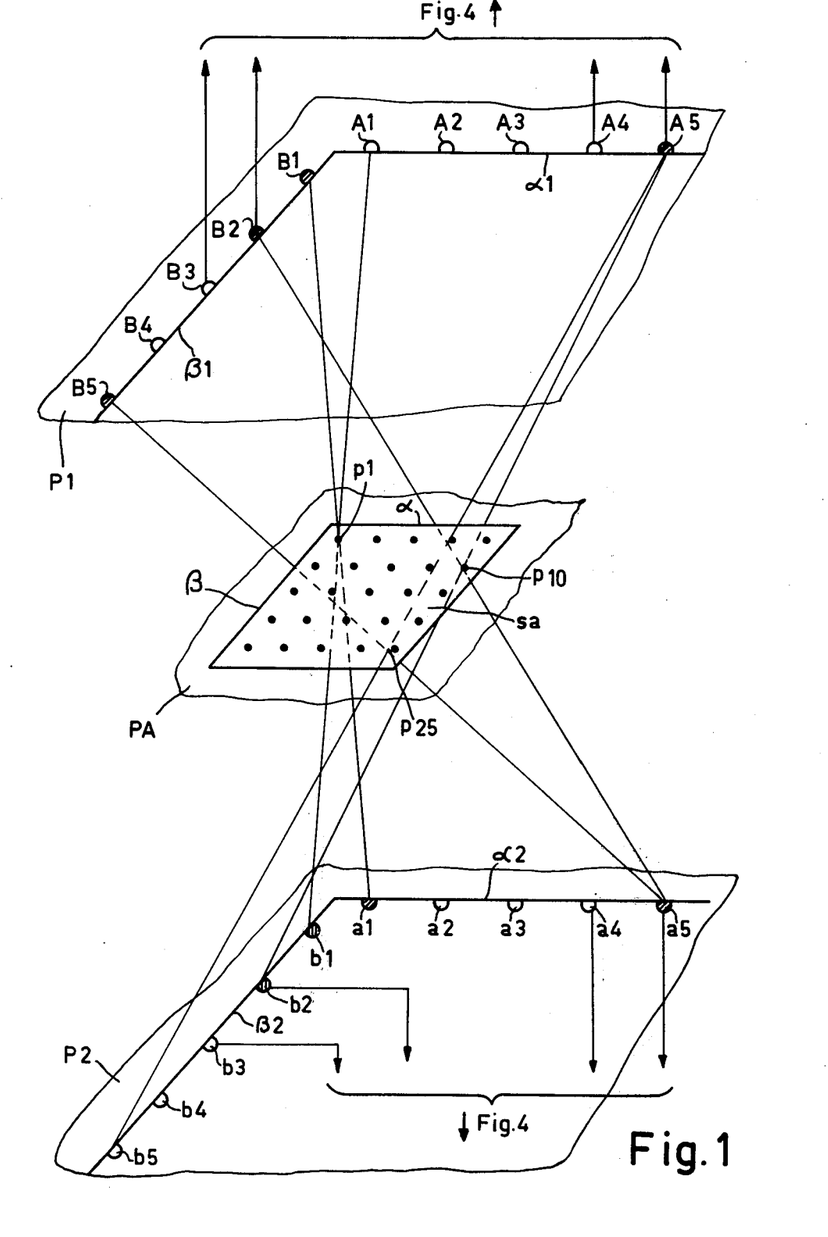
FIG. 1 shows a first arrangement in accordance with the invention for the formation of two examination lines which intersect each other at a point to be examined.

FIG. 1 shows a first arrangement wherein the detectors are arranged in two planes P1 and P2 which are parallel to a median plane of examination PA, the detectors being arranged one on each side of this plane at the same distance therefrom. The said detectors are evenly distributed between the two planes, for example, — as is shown in the drawing — 10 detectors A1 . . . A5, B1 . . . B5 in the plane P1 and ten detectors $a$ . . . $a5$, $b1$ . . . $b5$ in the plane P2. In each plane the detectors are divided between two straight lines which are parallel to each other ($\beta1$ is perpendicular to $\alpha_1$ in the plane P1; $\beta2$ is perpendicular to $\alpha_2$ in the plane P2) and the straight lines of the two planes are symmetrical with respect to the examination plane PA, their projections coinciding with two sides $\beta$ and $\alpha$ of the surface $sa$ to be examined. Moreover, the detectors are symmetrically distributed between the straight lines with respect to the examination plane (consequently, A1 is symmetrical with respect to $a1$, A5 with respect to $a5$, B5 with respect to $b5$, etc). Each point of the plane of examination is identified by localization in this plane by the intersection of two examination lines; the point $p1$ is thus situated at the point of intersection of two lines, one of which connects the detectors A1 and $b1$ whilst the other one connects the detectors B1 and $a1$ (the point $p10$ is situated at the intersection of the lines which connect A5 and $b2$ and B2 and $a5$; the point $p25$ is situated at the intersection of the lines which connect A5 and $b5$ and B5 and $a5$). Thanks to the symmetry of the system, an examination plane of $n = p1 \times p2$ regularly distributed points with a distance $e/2$ from each other is defined when the detectors are regularly distributed between the straight lines at a distance $e$ from each other, $n1$ and $n2$ being the numbers of detectors situated on the straight lines $\alpha1$ or $\alpha2$ and $\beta1$ or $\beta2$, respectively. $p1$ preferably equals $p2$. Generally, the two examination lines which enable the localization of one point connected two first detectors situated on the straight lines $\alpha1$ and $\beta1$ and the two second detectors which are symmetrically situated with respect to the first detectors, the plane PA being the symmetry plane, and on the straight lines $\alpha2$ and $\beta1$.

Figure 2:
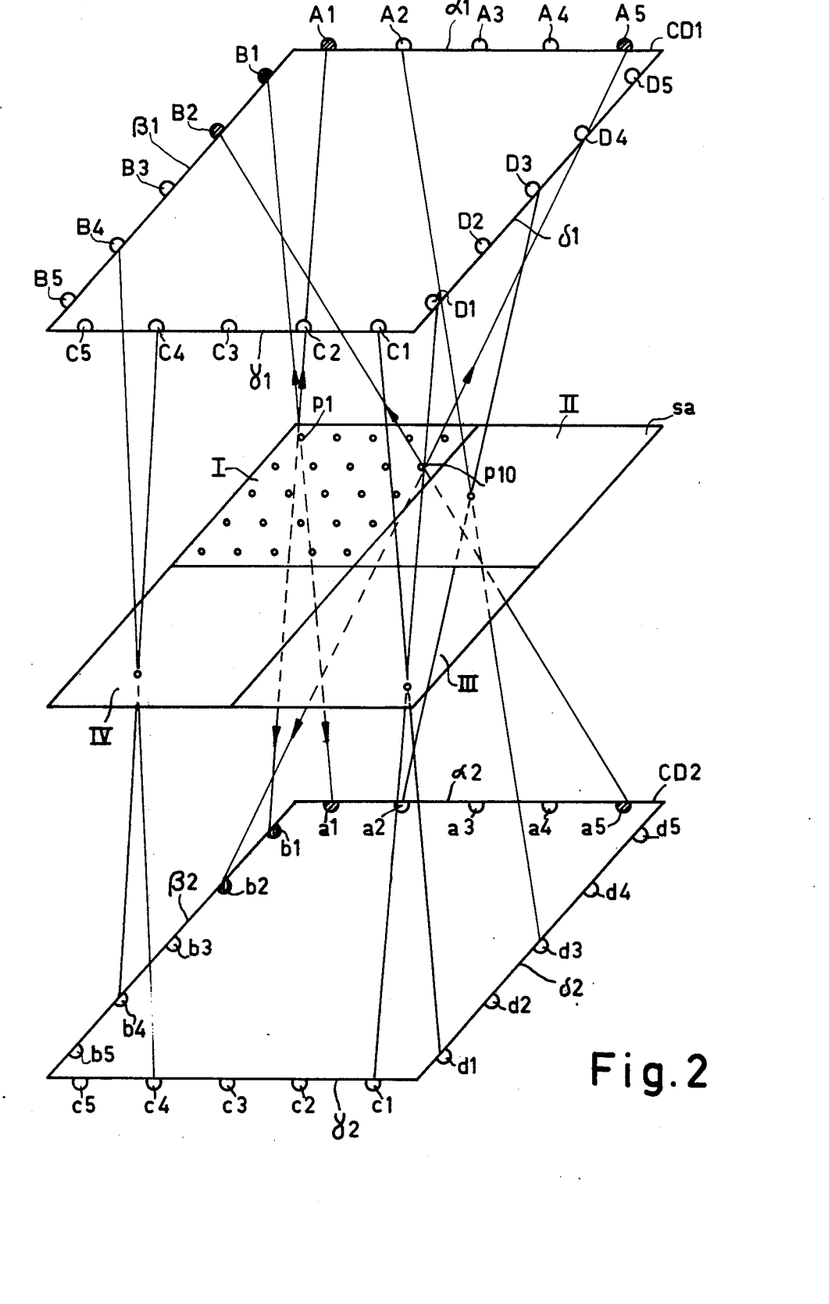
FIG. 2 shows an alternative for the arrangement shown in FIG. 1.

An alternative for this first arrangement consists in the distribution of the detectors, in each plane, between four straight lines which are perpendicular with respect to each other and which thus forms a rectangle, the projection of which in the plane PA limits the surface to be examined thereby. Consequently, if two rectangles are used, formed by the sides: $-\alpha1$, $\beta1$, $\gamma1$ (opposite $\alpha1$) $\delta1$ (opposite $\beta1$) for the plane P1, $-\alpha2$, $\beta2$, $\gamma2$ (opposite $\alpha2$), $\delta2$ (opposite $\beta2$) for the plane P2, and if the numbers of detectors are equal to $p1$ on $\alpha1$, $\alpha2$, $\gamma1$, $\gamma2$ and $p2$ on $\beta1$, $\beta2$, $\delta1$, $\delta2$, a system will be defined which enables identification in the plane PA of 4 ($p1.p2$). If furthermore $p1$ equals $p2$ (for example, $p/4$ detectors per side of a rectangle), the number of $n$ points to be identified equals $p^2/4$. This is shown in FIG. 2, wherein the surface SA to be examined is subdivided, for the sake of clarity, into four quadrants, each of which covers one fourth of the surface area. Each side of a rectangle (CD1 and CD2) comprises, for example, five detectors, thus defining twenty-five points to be identified per quadrant. The points 1 to 25 (quadrant I) are identified by the examination lines which connect the detectors of the sides $\alpha1$, $\beta1$ and $\beta1$, $\alpha2$; the points 26 to 50 (quadrant II) are identified by the examination lines which connect the detectors of the sides $\alpha1$, $\delta2$, and $\delta1$, $\alpha2$; the points 51 to 75 (quadrant III) are identified by the lines which connect the detectors of $\delta1$, $\gamma2$, and $\gamma1$, $\delta2$, and the points 76 to 100 (quadrant IV) are identified by the lines which connect the detectors of $\gamma1$, $\beta2$ and $\beta1$, $\gamma2$. The table I given hereafter, illustrates the combinations of intersecting lines which are used at a level of the plane of examination for the identification of the points of the surface to be examined.

The system in accordance with the invention thus favour the operation of the sources in the plane PA at the intersection of two intersecting lines.

Figure 3:
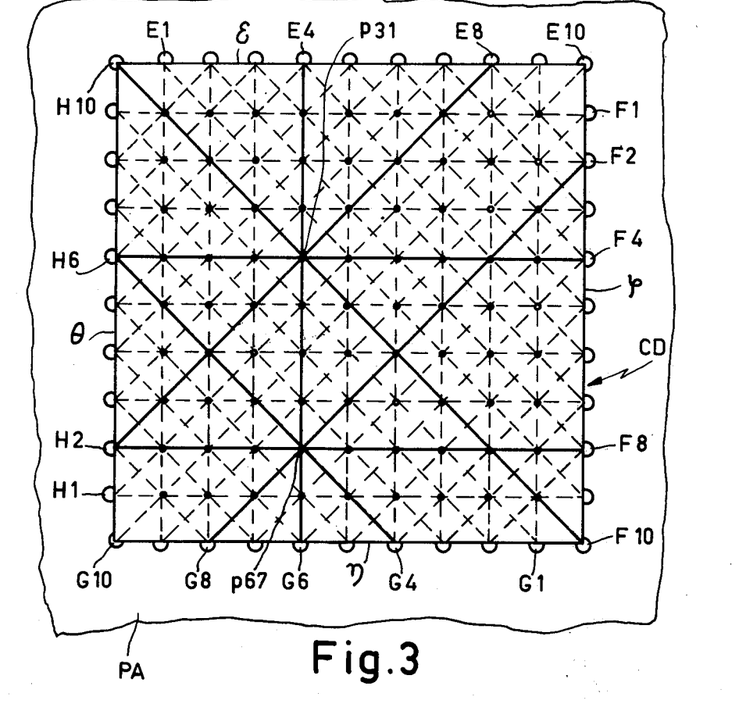
FIG. 3 shows a second arrangement, again in accordance with the invention, for the formation of four intersecting examination lines by the point to be examined.

FIG. 3 shows a second arrangement in accordance with the invention. According to this arrangement, the detectors E1 . . . E$p$ (E10 in the drawing), F1 . . . F$p$, (F10 in the drawing), G1 . . . G$p$ (G10 in the drawing, (H1 . . . H$p$ (H10 in the drawing) are regularly and symmetrically distributed over the four sides $\epsilon$, $\phi$, $\eta$, $\theta$, respectively, of a rectangle CD which is situated in a plane which coincides with the plane of examination PA. The surface to be examined is situated within the rectangle CD, and each point of this surface to be identified is situated at the intersection of four intersecting examination lines (the latter are represented by broken lines; they actually coincide with the straight lines which are parallel to the sides of the rectangle and which connect the detectors of two opposite sides, and with the straight lines which are parallel to two diagonals which connect the detectors of two adjoining sides). For example, the point $p31$ in FIG. 3 is localized at the intersection of the four examination lines which connect E4 to G6, H6 to F4, H10 to F10 and H2 to E8, respectively, and the point $p67$ is localized at the intersection of the four examination lines which connect E4 to G6, H2 to F8, G8 to F2, H6 to G4, respectively (the said eight examination lines are represented by non-interrupted lines). The table II given hereafter illustrates the combinations of the intersecting lines which are used for identifying the points of the surface to be examined. The system facilitates the operation of the sources situated at the intersection of four given examination lines. If the numbers of detectors on $\epsilon$ and $\eta$ on the one side and $\phi$ and $\theta$ on the other side equal $(p'+1)$ and $(p''+1)$ respectively, in total for example $[2(p'+1 p'')] +4$, the number of points to be identified equals $p'p''$, $p'$ preferably being equal to $p''$.

Figure 4:
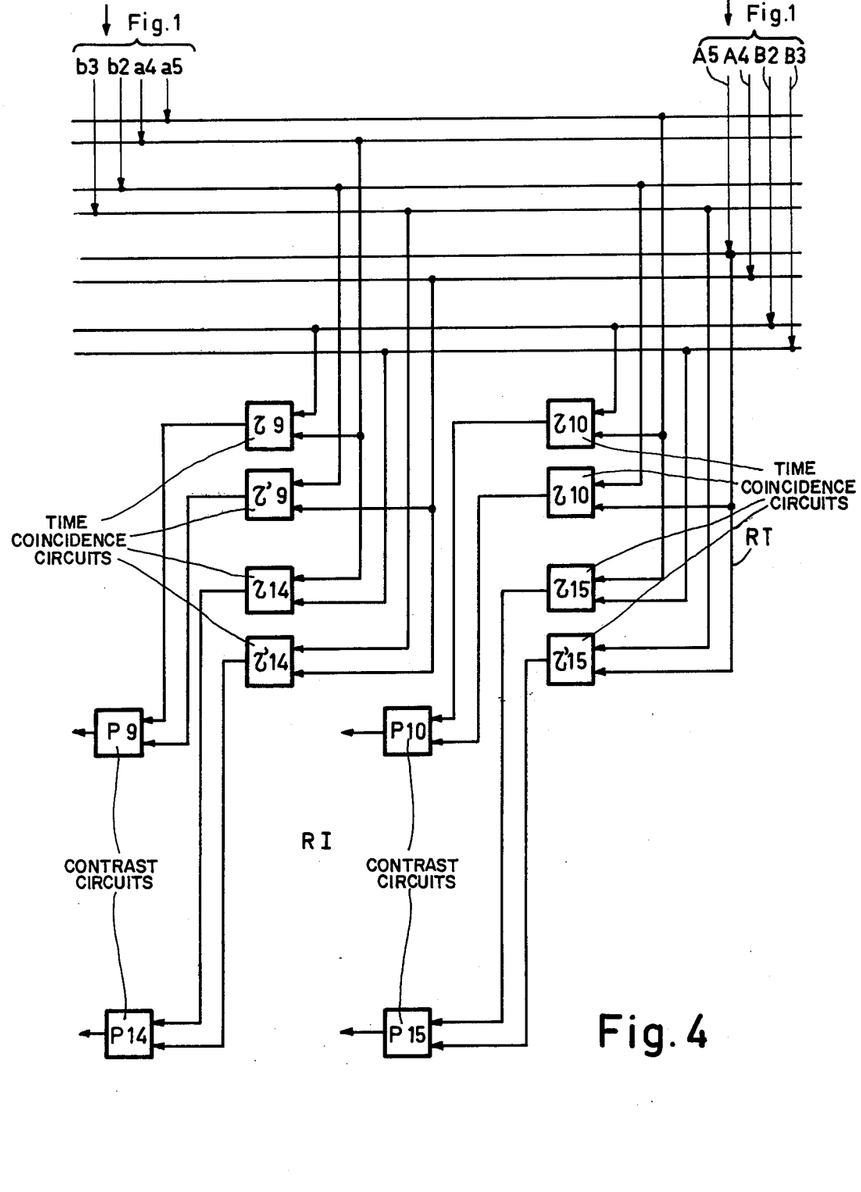
FIG. 4 shows a block diagram of part of the electronic circuitry to be used for the embodiment described with reference to the FIGS. 1 or 2.

FIG. 4 shows a section of the interconnected treatment circuits for the case corresponding to the arrangement shown in FIG. 1 (or 2). These circuits mainly comprise a network RT of $2n$ time coincidence circuits (50 gates in the case of FIG. 1, two hundred gates in the case of FIG. 2) and a network RI of $n$ identification circuits. The drawing shows only four contrast circuits P9, P10, P14, P15 and eight time coincidence circuits $\tau9$, $\tau'9$, $\tau10$, $\tau'10$, $\tau14$, $\tau'14$, $\tau15$, $\tau'15$ (coincidence period: $\tau'$) This part of the circuits on the one hand enables the identification of the points $p9$, $p10$, $p14$, $p15$, and on the other hand to contrast the image of these points if they are radio-active, the said points being situated (in accordance with FIG. 1) at the intersection of the examination lines which connect the detectors:

- A4 and b2, B2 and a4 (point p9)
- A5 and b2, B2 and a4 (point p10)
- A4 and b3, B3 and a4 (point p14)
- A5 and b3, B3 and a5 (point p15)

The signals originating from a group of two detectors for an examination line are applied (after conventional treatment: amplification, amplitude selection for the separation of the light flash) to the input of a coincidence circuit of the network RI; the signals originating from A4 and b2 are applied, for example, to the input of $\tau'p$, whilst those of a4 and B2 are applied to the input of $\tau 9$. The circuits such as $\tau 9$ and $\tau'9$ can consist of tunnel diodes which operate in a few nanoseconds. If the detectors consist of scintillator crystals NaI which are connected to photomultipliers, the scintillation duration being 300 to 400 ns, the coincidence circuits are blocked for this period of time after the recording of the beginning of the scintillations, and the above values are compatible with the number of strikes which can be detected (this value does not exceed 25,000 strikes per second per detector).

The signals supplied in coincidence by $\tau 9$ and $\tau'9$ are applied to the input of the contrast circuit P9 which corresponds to the point p9. The same reasoning can be followed for each of the three other contrast circuits shown in FIG. 4.

The contrast action obtained by means of the circuits such as P9 is a consequence of the design of these circuits. This is because the circuits are designed such that they supply the product or an equivalent of the product of the number of strikes detected in time coincidence by each of the two circuits $\tau$ and $\tau'$ coupled to their input; this takes place during successive periods which equal T.

The circuits P can be manufactured in accordance with different methods which will be briefly described hereinafter, without a detailed diagram being given. If it is anticipated that only few strikes can be detected during the time coincidence period $\tau$, for example, when $x\tau$, $x$ being the number of strikes, is small with respect to 1, the circuits P can consist of a simple time coincidence circuit whose validation time T corresonds to the image integration time, which then results in a technically simple approximation method for obtaining the product. The coincidence probability Z, during the time T, of strikes in numbers $x$ and $x'$, originating from two T independent origins, satisfies a formula derived from the Poisson distribution:

$$Z = 2(1 - e^{-xT})(1 - e^{-x'T}),$$

which can be approximated by $$T = 2T x x'$$

when T approximates 0. In this case T can be selected, for example, in the order of 0.1 second for values of $x$ and $x'$ of a few hundred strikes.

In a second embodimeent use can be made of analog circuits. The signals originating from the time coincidence circuits can accumulate their charge on any of the two (or four) relevant paths for a period T which may be equal to one second, and the product can then be obtained by means of a network consisting of operational amplifiers of the summing type and multipliers, which leads to the desired result by the following operations:

$$\frac{(X + X')^2 - (X - X')^2}{4} = XX',$$

X and X' being the charges equivalent to the numbers of strikes $x$ and $x'$ detected during the period T.

A third embodiment can utilize logarithmic amplifiers for each of the values $x$ and $x'$ and a summing device for adding the values thus obtained thereto.

A fourth embodiment utilizes digital compounds whereby a high accuracy during counting can be achieved; the strikes on the different paths are then stored in registers in a store for a period T, and a product is formed by a multiplier.

Regardless of the solution chosen, the multiplication is advantageous to demonstrate the differences in radioactivity in the zones of high radio-active density. This operation can be controlled, either by simply varying the value T, or by varying the amplification. Control is effected either for the entire plane of examination or only for a portion thereof.

Figure 5:
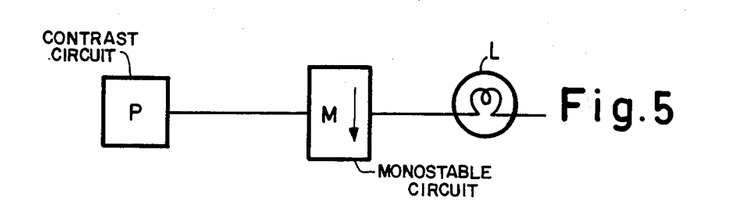
FIG. 5 shows a diagram of a display circuit for the point to be examined as an example of the means which can be used for the direct display of the radioactive image.

FIG. 5 shows a circuit for the display of a point to be examined as an example of the means which can be used for the direct display of the image. Each point is rendered "visible" via a micro-incandescent lamp L which, in a panel of $n$ lamps, occupies the position which corresponds to that of the said point in the plane of examination. After each period T, the "product" signal supplied by the circuit P actuates a monostable circuit M which provides power supply for the lamp L and whose period equals the maximum at T and is a function of the level of the said signal. This method results in the application of a voltage to a direct current lamp for a period of time which is a function of the product of the numbers of strikes detected in time coincidence. Obviously, other methods can also be used to achieve that the light intensity of each lamp is a function of this product. Similarly, other methods can be used for displaying the image, inter alia by utilizing oscilloscope in known manner and intermediate scanning circuits.

The foregoing examples were given merely by way of example and they do not exclude any alternative for the described system — utilizing at least two intersecting examination lines for defining a radio-active point of examination whose image is the representation of the product of the number of strikes emitted by this point in the direction of these lines — from the scope of the invention.

TABLE I

| examination lines | | point of identifi- | examination lines | | point of identifi- |
| --- | --- | --- | --- | --- | --- |
| No 1 | No 2 | cation | No 1 | No 2 | cation |
| A1-b1 | B1-a1 | p1 | D5-c5 | C5-d5 | p51 |
| A2-b1 | B1-a2 | p2 | D5-c4 | C4-d5 | p52 |
| A3-b1 | B1-a3 | p3 | D5-c3 | C3-d5 | p53 |
| , | , | , | , | , | , |
| A1-b2 | B2-a1 | p6 | D4-c5 | C5-d4 | p56 |
| , | , | , | , | , | , |
| A1-b3 | B3-a1 | p11 | D3-c5 | C5-d3 | p61 |
| , | , | , | , | , | , |
| A1-b5 | B5-a1 | p21 | D1-c5 | C5-d1 | p71 |
| , | , | , | , | , | , |
| A5-b5 | B5-a5 | p25 | D1-c1 | C1-d1 | p75 |
| A1-d5 | D5-a1 | p26 | B1-c5 | C5-b1 | p76 |
| A2-d5 | D5-a1 | p27 | B1-c4 | C4-b1 | p77 |

TABLE I-continued

| examination lines | | point of identifi- | examination lines | | point of identifi- |
|---|---|---|---|---|---|
| No 1 | No 2 | cation | No 1 | No 2 | cation |
| A3-d5 | D5-a3 | p28 | B1-c3 | C3-b1 | p78 |
| A1-d4 | D4-a1 | p31 | B2-c5 | C5-b2 | p81 |
| A1-d3 | D3-a1 | p36 | B3-c5 | C5-b3 | p86 |
| A1-d5 | D5-a1 | p46 | B5-c5 | C5-b5 | p96 |
| A5-d5 | D5-a5 | p50 | B5-c1 | C1-b5 | p100 |

TABLE II

| Examination lines | | | | Point of identifi- |
|---|---|---|---|---|
| No 1 | No 2 | No 3 | No 4 | cation |
| E1-G9 | F1-H9 | E2-H8 | H10-F10 | p1 |
| E2-G8 | F1-H9 | E3-H7 | E1-F9 | p2 |
| E3-G7 | F1-H9 | E4-H6 | E2-F8 | p3 |
| E1-G0 | F2-H8 | E3-H7 | H9-G1 | p10 |
| E1-G9 | F3-H7 | E4-H6 | H8-G2 | p19 |
| E1-G9 | F4-H6 | E5-H5 | H7-G3 | p28 |
| E7-G3 | F9-H1 | F6-G4 | H8-G2 | p79 |
| E8-G2 | F9-H1 | F7-G3 | H9-G1 | p80 |
| E9-G1 | F9-H1 | F8-G2 | H10-F10 | p81 |

What is claimed is:

1. A tomography system for direct display of an image of a radio-active body in a defined examination plane PA of examination points utilizing gamma-radiation, comprising:
an array of gamma-radiation comprising:
an array of gamma-radiation detectors situated in a configuration so as to define an array of examination lines each having a gamma-radiation detector at opposing ends thereof, at least two of the examination lines intersecting at each of the examination points;
means for detecting time coincidence of strikes of gamma-rays at the detectors at the opposing ends of each examination line indicative of a pair of gamma rays originating at the corresponding examination point
means for generating a signal for each examination point proportional to the product of the number of time coincidence strikes detected at the two examination lines intersecting thereat; and
means for displaying the signals as an image of the plane of examination points.

2. A system as claimed in claim 1, characterized in that the detectors are arranged in a single plane which coincides with the examination plane PA.

3. A system as claimed in claim 1, wherein the detectors are distributed between two planes P1 and P2 which are parallel to the plane PA and which are situated one on each side of and at the same distance from the said plane PA, characterized in that the said detectors are regularly distributed in the two planes between at least two mutually perpendicular lines which are symmetrical — in the plane P1 — with respect to those situated in the plane P2 and the plane PA, the projections thereof on the latter coinciding at least partly with two sides of the surface of the said plane PA to be examined, the detectors also being symmetrically distributed between the lines with respect to the plane of examination, each point of the latter being localized as the point of intersection of two examination lines, a first examination line thereof connecting two first detectors which are situated on a straight line in the plane P1 and a straight line in the plane P2, respectively, the projections thereof on the plane PA being mutually perpendicular, and a second examination line thereof connecting two detectors which are symmetrically situated with respect to the former detectors as regards the said plane PA.

4. A system as claimed in claim 1, characterized in that the detectors in the planes P1 and P2 are distributed between four mutually perpendicular lines, the projections thereof in the plane PA bounding the surface of the said plane PA to be examined.

5. A system as claimed in claim 4, characterized in that each plane comprises $p$ detectors which are subdivided into four equal parts and which are arranged at the same distance from each other, a number of $n$ points of examination, which is equal to $p^2/4$, being situated at a distance equal to $e/2$ from each other.

6. A system as claimed in claim 1, characterized in that the detectors are distributed along the circumference of a rectangle which bounds the surface of the plane to be examined, each point to be examined being localized at the intersection of four examination lines.

7. A system as claimed in claim 1, characterized in that the points to be examined are divided into $p'$ columns and $p''$ rows with an intermediate space $e'$, each point being localized at the intersection of two examination lines which coincide with the lines of the column or the row whereto it belongs, and two examination lines which enclose an angle of 45° with the former lines, the rectangle comprising $[2(p' + p'') +4]$ detectors, i.e. $(p'+1)$ and $(p''+1)$ for two adjoining sides of this rectangle, an intermediate space $e'$ existing between the detectors $p'$ and $p''$.

8. A system as claimed in claim 1 characterized in that the means for generating a signal for each examination point comprises coincidence circuits having a variable validation time T which has been chosen as a function of the numbers of strikes which can be detected in time coincidence.

9. A system as claimed in claim 1, characterized in that the means for generating a signal for each examination point comprises a network of operational amplifiers of the summing and multiplying type which supplies an output signal which equals the product of the charges which are the equivalent of the numbers of strikes detected in time coincidence on the examination lines during the period T, the point of intersection thereof localizing the said point.

10. A system as claimed in claim 1, characterized in that the means for generating a signal for each examination point comprises a network of logic circuits which comprise mainly a multiplying device and registers wherein the strikes which are detected in time coincidence during the period T' examination lines whose intersection localizes the said point are stored.

11. A system as claimed in claim 10, characterized in that T' has a value in the order of one second.

12. A system as claimed in claim 1, characterized in that the means for displaying each of the $n$ points of the plane of examination consist of a panel of $n$ micro-incandescent lamps, each lamp being coupled to a contrast circuit for a point to be examined which occupies a position which corresponds to that of the lamp in the panel coupled therewith by a monostable control circuit having a period which is a function of a signal which is available at the end of time intervals T (or T'), and hence a function of the product of the numbers of the strikes detected in time coincidence.

* * * * *

UNITED STATES PATENT AND TRADEMARK OFFICE
CERTIFICATE OF CORRECTION

PATENT NO.  : 4,075,482
DATED       : February 21, 1978
INVENTOR(S) : JEAN ROBERT PERILHOU It is certified that error appears in the above-identified patent and that said Letters Patent are hereby corrected as shown below:

Column 3, line 19, "and ten detectors a...a5," should be
--and ten detectors a1...a5,--

Column 3, line 48, "of one point connected two first detectors" should be --of one point connect two first detectors--

Signed and Sealed this

Seventh Day of November 1978

[SEAL]

Attest:

RUTH C. MASON
Attesting Officer

DONALD W. BANNER
Commissioner of Patents and Trademarks